US005972014A

United States Patent [19]

Nevins

[11] Patent Number: 5,972,014

[45] Date of Patent: Oct. 26, 1999

[54] CRICO THYROTOMY PUNCH SET

[76] Inventor: Mark Nevins, 703 Driftwood Dr., Suisun City, Calif. 94585

[21] Appl. No.: 09/095,967

[22] Filed: Jun. 11, 1998

[51] Int. Cl.[6] .......... A61B 17/34

[52] U.S. Cl. .......... 606/185; 606/186; 606/187; 606/181; 604/164; 604/169; 604/185

[58] Field of Search .......... 606/185, 186, 606/187, 181, 182; 604/169, 105, 164, 185; 128/200.26, 200.29

[56] References Cited

U.S. PATENT DOCUMENTS 3,713,447 1/1973 Adair .......... 128/347
4,331,138 5/1982 Jessen .......... 606/185
5,267,965 12/1993 Deniega .......... 606/185
5,624,459 4/1997 Kortenbach et al. .......... 606/185

*Primary Examiner*—Michael Buiz
*Assistant Examiner*—Lien Ngo

[57] ABSTRACT

A thyrotomy punch set is provided including a housing having a bore formed along a central axis thereof. A punch includes a rod slidably situated within the bore of the housing with an outboard end and an inboard end. The outboard end of the punch is enlarged. Also included is a pair of springs for urging the outboard end of the punch outwardly of the housing such that the outboard end must be biased toward the housing.

18 Claims, 2 Drawing Sheets

28 24 30 16 12 14 26 34 18 4 4 32 22

CRICO THYROTOMY PUNCH SET

BACKGROUND OF THE INVENTION

1. Field of the Invention

The present invention relates to trachea related devices and more particularly pertains to a new crico thyrotomy punch set for preventing aspiration of a patient.

2. Description of the Prior Art

The use of trachea related devices is known in the prior art. More specifically, trachea related devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art trachea related devices include U.S. Pat. No. 4,520,810; U.S. Pat. No. 4,291,690; U.S. Pat. No. 3,991,765; U.S. Pat. No. 4,677,978; U.S. Pat. No. 4,969,454; and U.S. Pat. No. Des. 338,957.

In these respects, the crico thyrotomy punch set according to the present invention substantially departs from the conventional concepts and designs of the prior art, and in so doing provides an apparatus primarily developed for the purpose of preventing aspiration of a patient.

SUMMARY OF THE INVENTION

In view of the foregoing disadvantages inherent in the known types of trachea related devices now present in the prior art, the present invention provides a new crico thyrotomy punch set construction wherein the same can be utilized for preventing aspiration of a patient.

The general purpose of the present invention, which will be described subsequently in greater detail, is to provide a new crico thyrotomy punch set apparatus and method which has many of the advantages of the trachea related devices mentioned heretofore and many novel features that result in a new crico thyrotomy punch set which is not anticipated, rendered obvious, suggested, or even implied by any of the prior art trachea related devices, either alone or in any combination thereof.

To attain this, the present invention generally comprises a housing having an oval cross-sectional along an entire length thereof. The housing has a rectangular bore formed along a central axis thereof. An enlarged recess is formed in an outboard end thereof in communication with the rectangular bore. A pair of cylindrical conduits are each formed along a foci of the housing. An annular thumb holder is integrally coupled to an inboard end of the housing in coplanar relationship therewith. A lateral channel with a rectangular cross-section is formed through the foci of the housing adjacent to the inboard end. As shown in FIGS. 2 & 3, the lateral channel remains in communication with the pair of cylindrical conduits. Next provided is a punch including a rod having a rectangular cross-section. In operation, the punch is slidably situated within the bore of the housing with an outboard end and an inboard end. The outboard end of the punch has a generally conical tip with an oval cross-section along its entire length. Also included is a handle having an elongated strip coupled at a central extent thereof to the inboard end of the punch in perpendicular relationship therewith. As such, the handle is slidably situated within the lateral slot of the housing along the central axis thereof. The handle has an inner edge with a plurality of tight undulations formed therein and an outer edge with a pair of broad semi-circular cut outs formed therein. Finally, a pair of coil springs are each situated within an associated one of the cylindrical conduits of the housing. The coil springs each have a first end coupled to an end of the corresponding cylindrical conduit and a second end coupled to the handle. By this structure, the handle has a first unbiased orientation wherein the outboard end of the punch resides exterior of the enlarged recess of the housing. Further, the punch has a biased orientation wherein the outboard end of the punch resides interior of the enlarged recess.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new crico thyrotomy punch set apparatus and method which has many of the advantages of the trachea related devices mentioned heretofore and many novel features that result in a new crico thyrotomy punch set which is not anticipated, rendered obvious, suggested, or even implied by any of the prior art trachea related devices, either alone or in any combination thereof.

It is another object of the present invention to provide a new crico thyrotomy punch set which may be easily and efficiently manufactured and marketed.

It is a further object of the present invention to provide a new crico thyrotomy punch set which is of a durable and reliable construction.

An even further object of the present invention is to provide a new crico thyrotomy punch set which is susceptible of a low cost of manufacture with regard to both materials and labor, and which accordingly is then susceptible of low prices of sale to the consuming public, thereby making such crico thyrotomy punch set economically available to the buying public.

Still yet another object of the present invention is to provide a new crico thyrotomy punch set which provides in the apparatuses and methods of the prior art some of the advantages thereof, while simultaneously overcoming some of the disadvantages normally associated therewith.

Still another object of the present invention is to provide a new crico thyrotomy punch set for preventing aspiration of a patient.

Even still another object of the present invention is to provide a new crico thyrotomy punch set that includes a housing having a bore formed along a central axis thereof. A punch includes a rod slidably situated within the bore of the housing with an outboard end and an inboard end. The outboard end of the punch is enlarged. Also included is a pair of springs for urging the outboard end of the punch outwardly of the housing such that the outboard end must be biased toward the housing.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
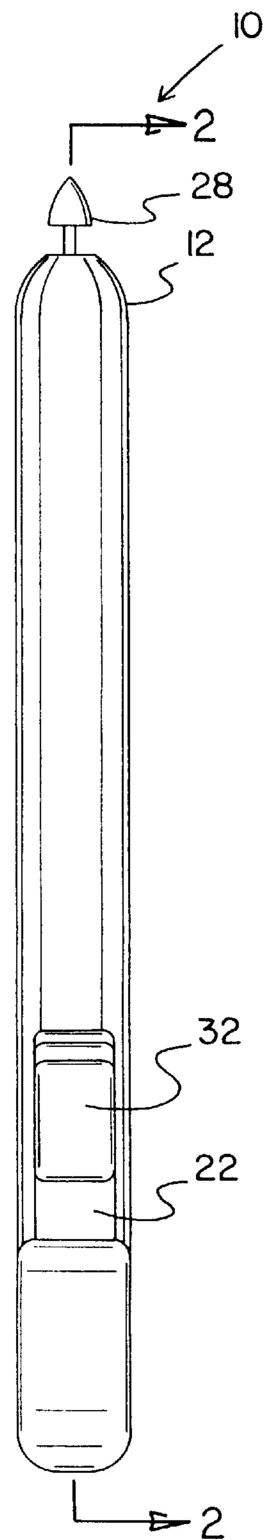
FIG. 1 is a side view of a new crico thyrotomy punch set according to the present invention.

With reference now to the drawings, and in particular to FIGS. 1 through 4 thereof, a new crico thyrotomy punch set embodying the principles and concepts of the present invention and generally designated by the reference numeral 10 will be described.

The present invention, designated as numeral 10, includes a housing 12 having an oval cross-sectional along an entire length thereof. The housing has a rectangular bore 14 formed along a central axis thereof. It should be noted that the rectangular bore may take any other suitable shape if desired. An enlarged recess 16 is formed in an outboard end of the housing in communication with the rectangular bore. For reasons that will become apparent hereinafter, the enlarged recess preferably has an oval configuration with a length and width greater than that of a cross-section of the rectangular bore. Preferably, the outboard end is tapered.

Figure 2:
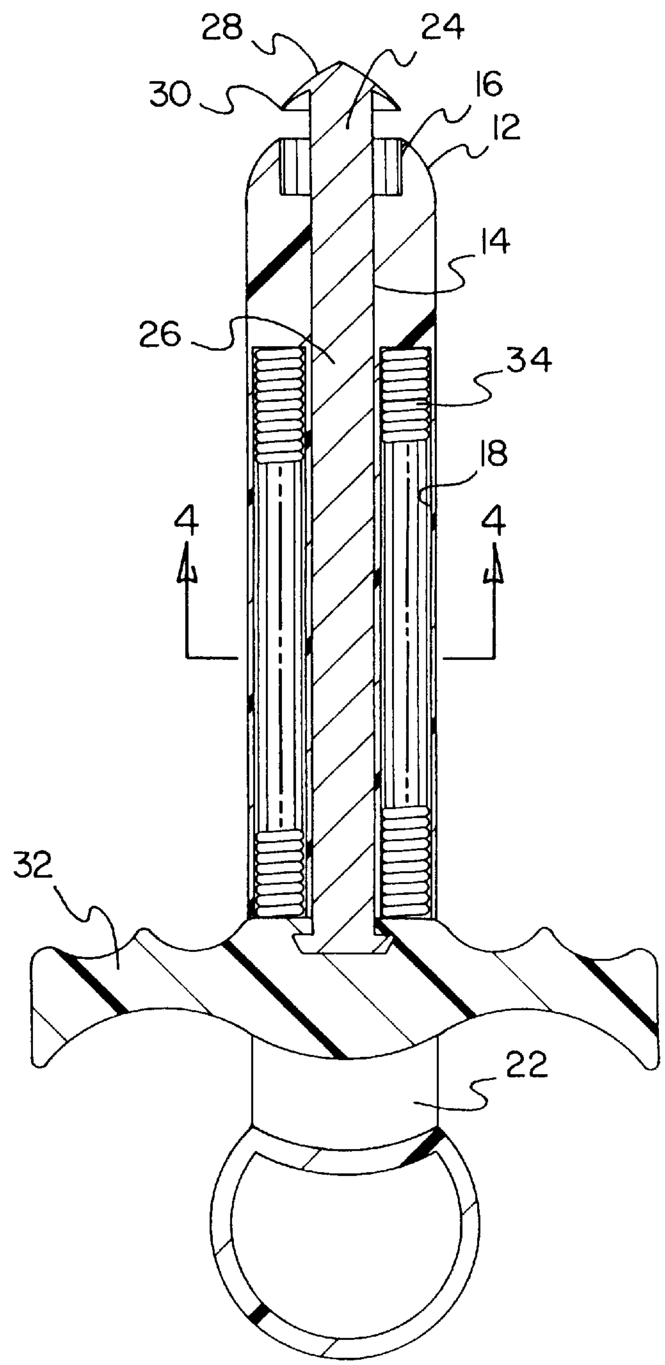
FIG. 2 is a cross-sectional view of the present invention taken along line 2—2 shown in FIG. 1 showing the punch in its relaxed orientation.
Figures 3, 4:
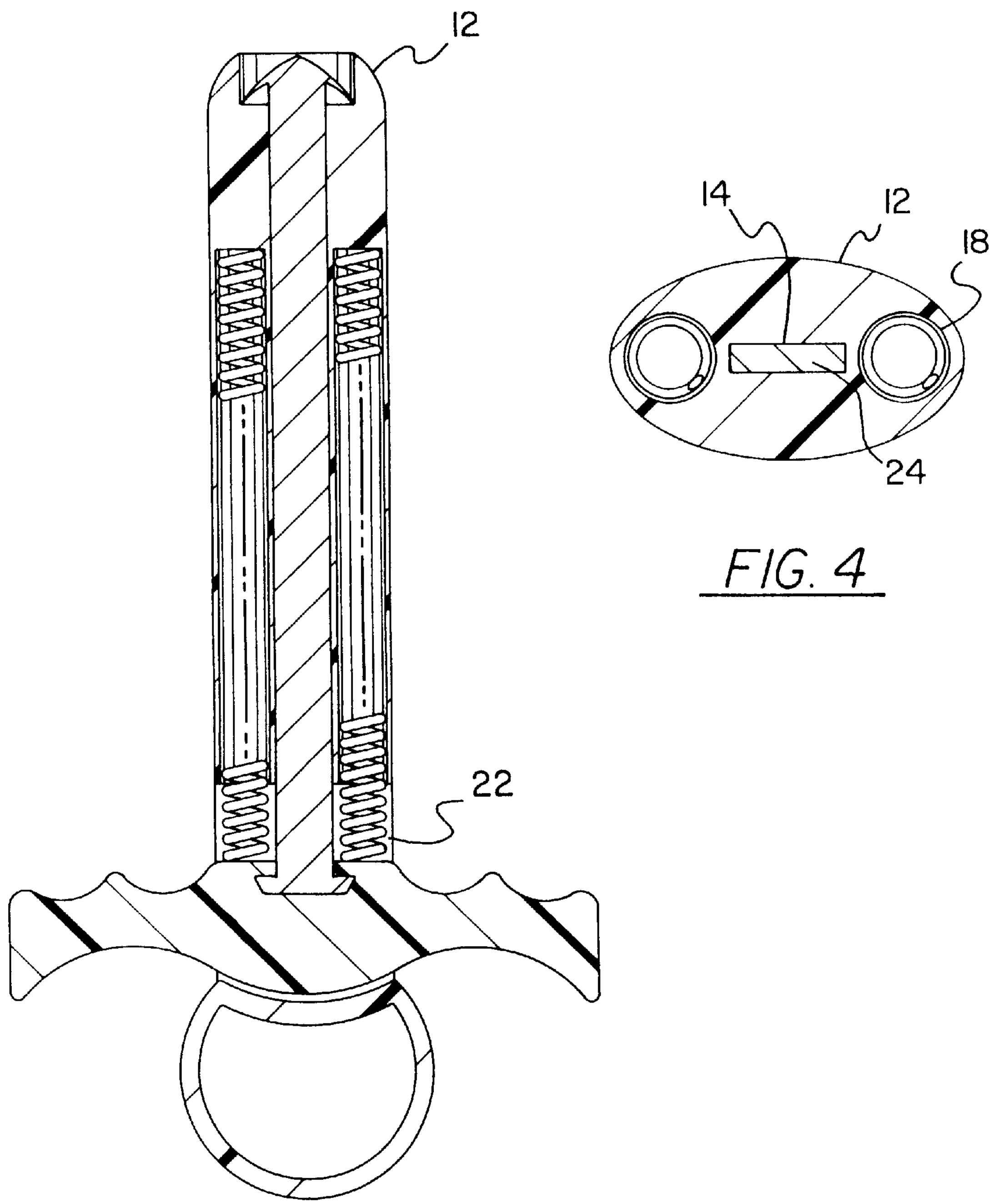
FIG. 3 is a cross-sectional view of the present invention showing the punch in its biased orientation.
FIG. 4 is a cross-sectional view of the present invention taken along line 4—4 shown in FIG. 2.

A pair of cylindrical conduits 18 are each formed along a foci of the housing. An annular thumb holder is integrally coupled to an inboard end of the housing in coplanar relationship therewith. A lateral channel 22 with a rectangular cross-section is perpendicularly formed through the foci of the housing adjacent to the inboard end next to the annular thumb holder. As shown in FIGS. 2 & 3, the lateral channel remains in communication with the pair of cylindrical conduits.

Next provided is a completely rigid metal punch 24 including a rod 26 having a rectangular cross-section. In operation, the punch is slidably situated within the bore of the housing with an outboard end 28 and an inboard end. The outboard end of the punch has a generally conical tip with an oval cross-section along its entire length. Optionally, the tip may be equipped with a round cross-section. As shown in FIGS. 2 & 3, the conical tip further includes a rearwardly extending lip 30 forming an extension of the tip and further a rear peripheral edge. Preferably, the tip has a depth equal to that of the recess.

Also included is a handle 32 having an elongated strip coupled at a central extent thereof to the inboard end of the punch in perpendicular relationship therewith. The handle preferably has a length less than ½ that of the housing. During use, the handle is slidably situated within the lateral slot of the housing along the central axis thereof. The handle has an inner edge with a plurality of tight finger undulations formed therein and an outer edge with a pair of broad semi-circular palm cut outs formed therein. An apex defined by the broad semi-circular cut outs is preferably received by an indentation formed in the annular thumb holder.

Finally, a pair of coil springs 34 are each situated within an associated one of the cylindrical conduits of the housing. The coil springs each have a first end coupled to an end of the corresponding cylindrical conduit and a second end coupled to the handle. The coil springs preferably extend along an entire length of the housing. By this structure, the handle has a first unbiased orientation wherein the outboard end of the punch resides exterior of the enlarged recess of the housing. Further, the punch has a biased orientation wherein the outboard end of the punch resides interior of the enlarged recess. During use, the present invention may be used by emergency personnel to ensure fragments of a trachea are pulled back away from the trachea to reduce risk of aspiration.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A thyrotomy punch set comprising, in combination:

a housing having an oval cross-sectional along an entire length thereof, the housing having a rectangular bore formed along a central axis thereof, an enlarged recess formed in an outboard end thereof in communication with the rectangular bore, a pair of cylindrical conduits each formed along the housing, an annular thumb holder integrally coupled to an inboard end of the housing, and a lateral channel with a rectangular cross-section formed through the housing adjacent to the inboard end, wherein the lateral channel is in communication with the pair of cylindrical conduits;

a punch including a rod having a rectangular cross-section slidably situated within the bore of the housing with an outboard end and an inboard end, the outboard end of the punch having a generally conical tip with an oval cross-section along its entire length;

a handle including an elongated strip coupled at a central extent thereof to the inboard end of the punch in perpendicular relationship therewith such that the handle is slidably situated within the lateral channel of the housing along the central axis thereof, the handle having a plurality of tight undulations formed therein and a pair of broad semi-circular cut outs formed therein; and a pair of coil springs each situated within an associated one of the cylindrical conduits of the housing, the coil springs each having a first end coupled to an end of the corresponding cylindrical conduit and a second end coupled to the handle, whereby the handle has a first unbiased orientation wherein the outboard end of the punch resides exterior of the enlarged recess of the housing and a biased orientation wherein the outboard end of the punch resides interior of the enlarged recess.

2. A thyrotomy punch set comprising:

a housing having a bore formed along a central axis thereof;

a punch including a rod slidably situated within the bore of the housing with an outboard end and an inboard end, the outboard end of the punch being enlarged; and means for urging the outboard end of the punch outwardly of the housing such that the outboard end must be biased toward the housing;

wherein a handle is coupled to the punch and a thumb holder is coupled to the housing.

3. A thyrotomy punch set as set forth in claim 2 wherein the punch is rigid.

4. A thyrotomy punch set as set forth in claim 2 wherein the handle has an inner edge with a plurality of tight undulations formed therein and an outer edge with a pair of broad semi-circular cut outs formed therein.

5. A thyrotomy punch set as set forth in claim 2 wherein the housing has an oval cross-section along a length thereof.

6. A thyrotomy punch set as set forth in claim 2 wherein the means includes at least one coil spring.

7. A thyrotomy punch set as set forth in claim 2 wherein the enlarged outboard end of the punch includes a generally conical tip.

8. A thyrotomy punch set comprising:

a housing having a bore formed along a central axis thereof;

a punch including a rod slidably situated within the bore of the housing with an outboard end and an inboard end, the outboard end of the punch being enlarged; and means for urging the outboard end of the punch outwardly of the housing such that the outboard end must be biased toward the housing;

wherein the housing has a substantially oval cross-section along a length thereof.

9. A thyrotomy punch set as set forth in claim 8 wherein the punch is rigid.

10. A thyrotomy punch set as set forth in claim 8 wherein a handle is coupled to the punch and a thumb holder is coupled to the housing.

11. A thyrotomy punch set as set forth in claim 10 wherein the handle has an inner edge with a plurality of tight undulations formed therein and an outer edge with a pair of broad semi-circular cut outs formed therein.

12. A thyrotomy punch set as set forth in claim 8 wherein the means includes at least one coil spring.

13. A thyrotomy punch set as set forth in claim 8 wherein the enlarged outboard end of the punch includes a generally conical tip.

14. A thyrotomy punch set comprising:

a housing having a bore formed along a central axis thereof, the housing having an end with a recess formed therein with a width greater than that of the bore; and a punch including a rod slidably situated within the bore of the housing with an outboard end and an inboard end, the outboard end of the punch having a width greater than that of the rod and adapted for being removably positioned within the recess of the housing such that a peripheral edge of the outboard end engages a bottom surface of the recess;

wherein a handle is coupled to the punch and a thumb holder is coupled to the housing.

15. A thyrotomy punch set as set forth in claim 14 wherein the punch is rigid.

16. A thyrotomy punch set as set forth in claim 14 wherein the handle has an inner edge with a plurality of tight undulations formed therein and an outer edge with a pair of broad semi-circular cut outs formed therein.

17. A thyrotomy punch set as set forth in claim 14 and further including means for urging the outboard end of the punch outwardly of the housing such that the outboard end must be biased toward the housing.

18. A thyrotomy punch set as set forth in claim 14 wherein the enlarged outboard end of the punch includes a generally conical tip.

* * * * *